(12) United States Patent
Knutson et al.

(10) Patent No.: US 8,547,533 B2
(45) Date of Patent: Oct. 1, 2013

(54) COMPOSITE PROBES AND USE THEREOF IN SUPER RESOLUTION METHODS

(75) Inventors: Jay R. Knutson, Kensington, MD (US); Gary L. Griffiths, North Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/519,737

(22) PCT Filed: Dec. 28, 2010

(86) PCT No.: PCT/US2010/062214
§ 371 (c)(1),
(2), (4) Date: Jun. 28, 2012

(87) PCT Pub. No.: WO2011/090710
PCT Pub. Date: Jul. 28, 2011

(65) Prior Publication Data
US 2012/0309045 A1     Dec. 6, 2012

Related U.S. Application Data

(60) Provisional application No. 61/290,282, filed on Dec. 18, 2009.

(51) Int. Cl.
*G01C 3/12* (2006.01)

(52) U.S. Cl.
USPC .... 356/16; 250/458.1; 250/459.1; 536/25.32; 436/139; 436/164; 436/172; 356/951; 356/432

(58) Field of Classification Search
None
See application file for complete search history.

(56) References Cited

U.S. PATENT DOCUMENTS

| | | |
|---|---|---|
| 5,731,588 A | 3/1998 | Hell et al. |
| 5,866,911 A | 2/1999 | Baer |
| 5,952,668 A | 9/1999 | Baer |
| 6,177,414 B1 | 1/2001 | Tomalia et al. |
| 6,259,104 B1 | 7/2001 | Baer |
| 6,372,907 B1 | 4/2002 | Lee et al. |
| 6,891,670 B2 | 5/2005 | Gugel et al. |
| 6,903,347 B2 | 6/2005 | Baer |
| 6,934,079 B2 | 8/2005 | Hell et al. |
| 7,064,824 B2 | 6/2006 | Hell |
| 7,071,477 B2 | 7/2006 | Baer |
| 7,115,885 B2 | 10/2006 | Hell |
| 7,253,893 B2 | 8/2007 | Hell et al. |
| 7,394,077 B2 | 7/2008 | Baer |
| 7,430,045 B2 | 9/2008 | Hell |
| 7,535,012 B2 | 5/2009 | Betzig et al. |
| 7,538,893 B2 | 5/2009 | Hell et al. |
| 7,539,115 B2 | 5/2009 | Hell |
| 7,566,783 B2 | 7/2009 | Lakowicz |
| 2003/0092005 A1 | 5/2003 | Levene et al. |
| 2005/0064604 A1 | 3/2005 | Bohmann et al. |
| 2006/0182687 A1 | 8/2006 | Yang et al. |
| 2006/0252079 A1* | 11/2006 | Oldham et al. ............ 435/6 |
| 2008/0032414 A1 | 2/2008 | Zhuang et al. |
| 2008/0068588 A1 | 3/2008 | Hess et al. |
| 2008/0068589 A1 | 3/2008 | Hess et al. |
| 2008/0070322 A1 | 3/2008 | Hess et al. |
| 2008/0070323 A1 | 3/2008 | Hess et al. |
| 2008/0111086 A1 | 5/2008 | Betzig et al. |
| 2008/0182336 A1 | 7/2008 | Zhuang et al. |
| 2009/0035800 A1 | 2/2009 | Aartsma et al. |
| 2009/0047699 A1 | 2/2009 | Graham |
| 2009/0121153 A1 | 5/2009 | Baer |
| 2009/0134342 A1 | 5/2009 | Hell et al. |
| 2009/0206251 A1 | 8/2009 | Hess et al. |

FOREIGN PATENT DOCUMENTS

| | | |
|---|---|---|
| WO | 2006078857 A2 | 7/2006 |
| WO | 2007030835 A2 | 3/2007 |
| WO | 2008098144 A1 | 8/2008 |
| WO | 2009024529 A1 | 2/2009 |

OTHER PUBLICATIONS

Deng et al.; "Saturated Forster Resonance Energy Transfer Microscopy with a Stimulated Emission Depletion Beam: A Pathway Toward Single-Molecule Resolution in Far-Field Bioimaging"; Optic Letters; 35(23); (2010).
Huang et al; "Super-Resolution Fluorescence Microscopy"; Annu. Rev. Biochem; 78; pp. 993-1016; (2009).
International Search Report and Written Opinion; International Application No. PCT/US2010/062214; International Filing Date Dec. 28, 2010; Date of Mailing Sep. 8, 2011; Applicant's File Reference No. NIH0036PCT, NIH0036US2; 10 pages.
Kobayashi et al.; "New Strategies for Fluorescent Probe Design in Medical Diagnostic Imaging"; Cham. Rev.; 110; pp. 2620-2640; (2010).
Rust et al.; "Sub-diffraction-limit Imaging by Stochastic Optical Reconstruction Microscopy (STORM)"; Nature Methods; 3(10); pp. 793-795; (2006).
Schuler et al.; "Polyproline and the "Spectroscopic Ruler" Revisited with Single-Molecule Fluorescence"; PNAS; 102(8); pp. 2754-2759; (2005).
Subach et al.; "Red Fluorescent Protein with Reversibly Photoswitchable Absorbance for Photochromic FRET"; Chemistry & Biology; 17; pp. 745-755; (2010).

* cited by examiner

*Primary Examiner* — Jon P Weber
*Assistant Examiner* — Chunyuan Luo
(74) *Attorney, Agent, or Firm* — Cantor Colburn LLP

(57) ABSTRACT

Composite probes for super resolution optical techniques using super resolution via transiently activated quenchers (STAQ) include a donor moiety and an acceptor moiety joined by a linker, wherein the acceptor moiety, when excited by incident radiation, is excited to a state which, for example, absorbs in the donor emission region, such that the acceptor moiety in its excited state quenches at least a portion of the donor moiety emission. Other transiently activated quenching mechanisms and moieties could accomplish the same task by reducing donor population. Also disclosed are methods for irradiating a selected region of a target material including the composite probe, wherein the composite probe enables improved resolution by point spread function modification and/or nanoscale chemical reactions.

40 Claims, 5 Drawing Sheets

COMPOSITE PROBES AND USE THEREOF IN SUPER RESOLUTION METHODS

CROSS-REFERENCE TO RELATED APPLICATIONS

This application is a 371 of PCT/US2010/062214 filed Dec. 28, 2010, which claims the benefit of priority to U.S. provisional application No. 61/290,282, filed on Dec. 28, 2009, under provisions of 35 U.S.C. 119 and the International Convention for the protection of Industrial Property, which are incorporated herein by reference.

STATEMENT OF GOVERNMENT SUPPORT

This invention was made in part with government support from the National Institutes of Health. The government has certain rights in this invention.

BACKGROUND

Fluorescence microscopy is an important tool in the biomedical sciences allowing for the imaging of biological cells and tissues. One limit of fluorescence microscopy is that the optics of a microscope cannot create illuminated spots smaller than the diffraction limit, thus limiting the usefulness of such techniques to image biological samples at high resolution, generally below about 200 nm for visible light. The term 'Superresolution microscopy', also referred to as sub-diffraction limit microscopy, refers to techniques suitable for imaging objects smaller than about 200 nm.

One of the most well known Super Resolution Microscopy techniques is the stimulated emission depletion technique (STED) developed by Dr. Stefan Hell. The STED technique is a nonlinear optics technique using two laser pulses in which a first diffraction limited pulse excites fluorophores in a spot and a second "donut profile" overlapping pulse stimulates emission while simultaneously driving the fluorophores back to the ground state, effectively depleting the edges of the diffraction limited spot while allowing the center of the original spot to fluoresce. The result is a narrowed point spread function that has been shown to provide spot sizes of 20 nm or less, allowing for resolution of structures well below the diffraction limit. Typical fluorescent dyes used in STED include ATTO 647N and ATTO 655. One disadvantage of the STED technique is that large powers are generally required to narrow the point spread function, potentially damaging biological samples and limiting its usefulness.

Additional Super Resolution Microscopy techniques include stochastic optical reconstruction microscopy (STORM) and photo-activated localization microscopy (PALM). Both STORM and PALM use photoactivatable probes that are activated by light. Because photoactivation is stochastic, only a few, well-separated (spaced beyond Rayleigh criterion/Abbe limit) molecules are photoactivated with each pulse of light. After registration (through repeated luminescence excitation/emission cycles) and photobleaching of the activated spots, another flash of photoactivating light generates another different subpopulation of photoactivatable molecules. The process is repeated many times, fitting the point spread functions to obtain precise center loci and building up an image molecule-by-molecule, a "pointillist" approach. Because the molecules were localized at different times, the apparent resolution of the final image can be much higher than that limited by diffraction. A drawback of both STORM and PALM is that it may take several minutes or even hours to collect the data needed to produce images.

Super Resolution Microscopy techniques that allow for improved ultrafine imaging, particularly of living biological samples, would be desirable.

SUMMARY

In one embodiment, a composite probe comprises a donor moiety linked to an acceptor moiety with a linker, wherein the donor moiety produces a donor moiety emission when excited to a donor excited state by a first wavelength of incident radiation, and the acceptor moiety is effective to couple the donor and acceptor electromagnetically and quench at least a portion of the donor moiety emission when the acceptor moiety is separately excited to an acceptor excited state by a second wavelength of incident radiation.

In another embodiment, a method for irradiating a selected region of a target material comprising the composite probe described above comprises producing an exciting light beam in an optical device having a spot closely approximating its point spread function, the exciting light beam having a first wavelength in a region effective to excite the donor moiety of the composite probe to a donor excited state to produce a donor emission; producing a quenching light beam in the optical device, the quenching light beam having a second wavelength effective to excite the acceptor moiety of the composite probe to an acceptor excited state, wherein the acceptor moiety in the acceptor excited state is an excited quencher that quenches in the donor emission region; and directing the exciting light beam and the quenching light beam of radiation to overlap in the selected region of the target material to quench at least a portion of the donor emission of the donor moiety in the selected region, wherein the quenching produces a modified point spread function in the optical device that is narrower than the point spread function in the absence of the quenching beam.

In another embodiment, provided is a method for irradiating a selected region of a target material, the method comprises providing a target material comprising a donor molecule and an acceptor molecule, wherein the donor molecule is in an amount effective to produce a donor molecule emission when excited to a donor excited state by a first wavelength of incident radiation, and the acceptor molecule is in an amount effective to couple the donor and acceptor electromagnetically and quench at least a portion of the donor molecule emission when the acceptor is separately excited to an acceptor excited state by a second wavelength of incident radiation; producing an exciting light beam in an optical device having a spot closely approximating its point spread function, the exciting light beam having the first wavelength in a region effective to excite the donor molecule of the composite probe to a donor excited state to produce a donor emission; producing a quenching light beam in the optical device, the quenching light beam having the second wavelength effective to excite the acceptor moiety of the composite probe to an acceptor excited state, wherein the acceptor moiety in the acceptor excited state is an excited quencher that quenches in the donor emission region; and directing the exciting light beam and the quenching light beam of radiation to overlap in the selected region of the target material to quench at least a portion of the donor emission of the donor molecule in the selected region, wherein the quenching produces a modified point spread function in the optical device that is narrower than the point spread function in the absence of the quenching beam.

DETAILED DESCRIPTION

In many optics applications, a light beam is focused to the smallest possible spot size in a specimen in order to selectively photoexcite a molecular species, e.g., a fluorescent probe, in the illuminated spot. Such applications include scanning fluorescence microscopy, scanning microlithography, nanofabrication, and optical digital information storage and retrieval. The lenses in such demanding high-resolution applications often approach diffraction-limited performance. The STAQ methodology disclosed herein is a new super resolution technique for point spread function engineering, i.e., spot size reduction, in optics applications.

Figure 1:
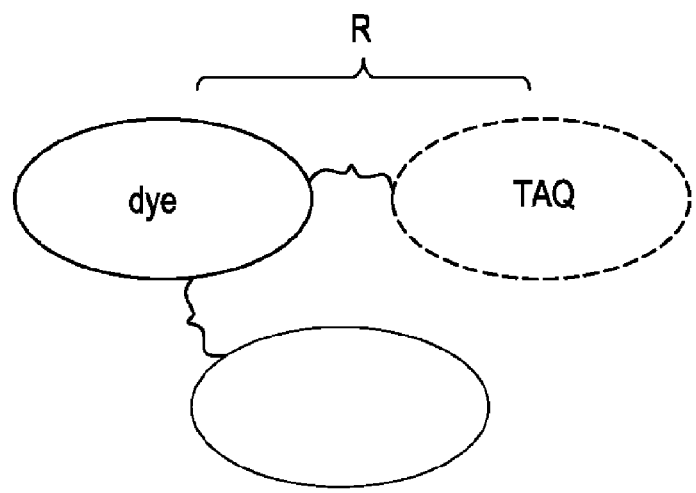
FIG. 1 shows one embodiment of super resolution via transiently activated quenchers (STAQ) donor and transiently activated quencher (TAQ). The dye is held within FRET distance of one or more TAQ by a linker (R<Ro) but the FRET is not due to overlap between 1'->0' emission of dye and 0->1 absorbance of TAQ; it is between 1'->0' of dye and the transient absorbance of TAQ moiety (1'->2(n)'). In the Jablonski diagram at right, hollow arrows are transient absorbance, gray arrows are excitation of dye and TAQ. Superscript ' denotes relaxed states and curved arrows represent relaxation leading to a Stokes shift. Energy levels are actually often broad so one or more TAQ may quench various colors of dye.
Figure 1:
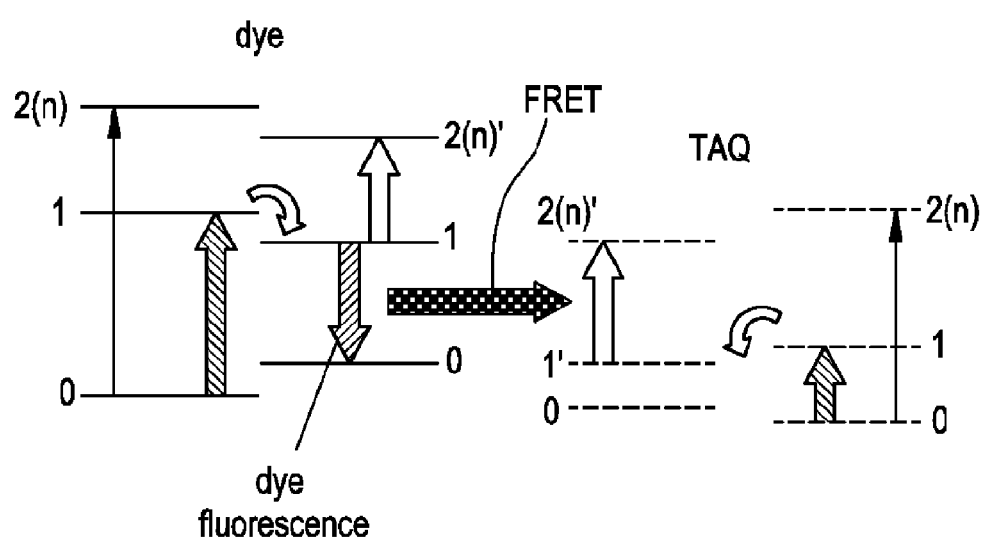
Figure 2:
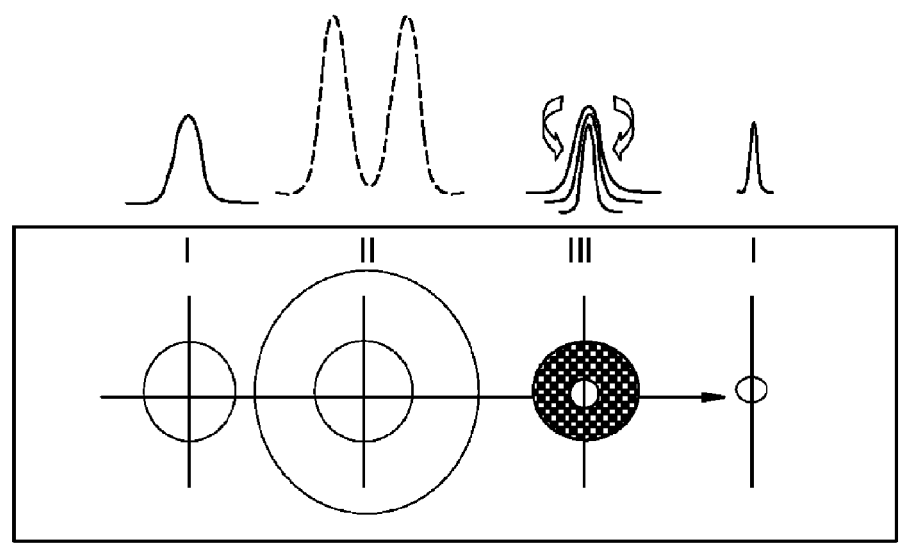
FIG. 2 illustrates the proposed mechanism of superresolution by TAQ. Original excited dye population generated by psf, I. "Donut profile" excitation of TAQ moiety II. Portions of I strongly quenched by excited TAQ, III (hatched). Resulting excited dye profile IV. Bar, approximate wavelength of light exciting dye or TAQ.
Figure 3:
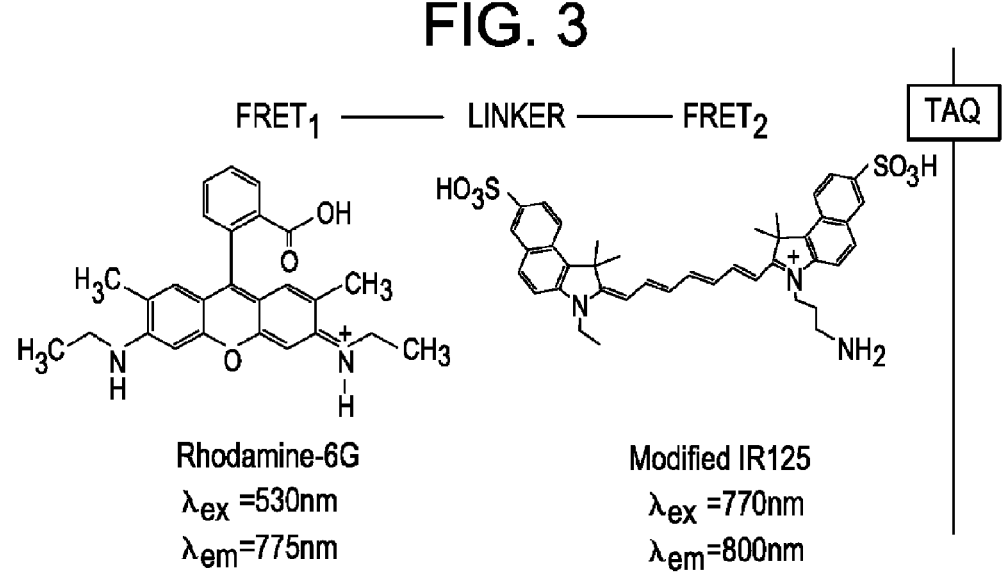
FIG. 3 shows an exemplary composite probe.

The STAQ methodology is a super resolution optics technique wherein a composite probe, e.g., a novel kind of FRET pair separated by a linker, is used to narrow the point spread function of a probe population within an exciting light beam and thus the spot size of, for example, a fluorescence microscope. The composite probe is comprised of a donor moiety and a transiently activated quencher (TAQ) (e.g., acceptor) joined by a linker such as a polyproline. (FIG. 1) In one example, the transiently activated quencher, in its ground state, does not absorb in the emission band region of the donor, however, the transiently activated quencher in its excited state absorbs significantly in the donor emission region. In the STAQ technique, the donor excitation light beam excites the donor moiety and the quenching light beam excites the transiently activated quencher moiety, effectively shutting off a portion of the donor emission by a quenching mechanism that may pass across or through the linker. (FIG. 2) Instead of point spread function engineering by stimulated emission as in STED, the composite dyes of the STAQ technique provide point spread function engineering by a composite excitation/quench process. A particular feature of this first type of STAQ composite probes is that the transiently activated quencher absorbs significantly in the donor emission region primarily when the TAQ is in its excited state, not in its ground state. As used herein, the term excited state includes, but is not limited to, singlet and triplet states of the donor and acceptor moieties. In addition, the term moiety includes chromophores, e.g., dyes, as well as chromophore-ligand complexes such as metal-organic clathrate complexes and fluorescent proteins. An exemplary STAQ probe is shown in FIG. 3. Note that this STAQ process differs from normal FRET because the FRET process is essentially absent until the acceptor, and not just the donor, is excited.

In one embodiment, the acceptor moiety quenches the donor moiety by quenching a portion of the donor emission. "Quench" has its standard meaning and refers to a reduction in the yield of photons or other dye excitation sequelae in a moiety. For example, quench includes a reduction in the fluorescence intensity of a fluorescent group or moiety as measured at a specified wavelength, regardless of the mechanism by which the reduction is achieved. As specific examples, the quenching can be due to molecular collision, energy transfer such as FRET, photoinduced electron transfer such as PET, proton transfer (ESPT), a change in the fluorescence spectrum (color) of the fluorescent group or moiety, or another mechanism (or combination of mechanisms). Quenching can be dynamic quenching, i.e., collisional, or static quenching. In the case of a FRET pair, it is possible that all or many of the potential photons lost by the donor dye will subsequently convert to photons that will emit in the quencher emission band, yet the composite probe will still be 'quenched', that is, lose emission and/or excited population in the donor region where the donor would normally emit or sensitize chemical reactions. The quenching in the pertinent region may be accompanied by enhancement in another spectral region, but since only the "donor" region of the spectrum is being observed for superresolving purposes (or only the donor region is capable of triggering photopolymerization), the pertinent part of the spectrum is quenched.

The amount of the reduction is not critical and can vary over a broad range. A fluorescence signal is "substantially quenched" if its intensity at a specified wavelength is reduced by at least 50%, for example by 50%, 60%, 70%, 75%, 80%, 85%, 90%, 95%, 96%, 97%, 98%, 99% or even 100%.

In the disclosed methods, the TAQ is excited by a quenching light beam to quench at least a portion of the donor emission. In other words, the TAQ acts as a deactivating partner that prevents the donor from performing at least a portion of its role, e.g., fluorescing or photosensitizing reactions such as polymerization or etching or ligand release. While the quenching process is exemplified by transient absorption by the TAQ (a transiently absorbing quencher in this case), it should be understood that a variety of photophysical processes that exploit the difference between a ground and an excited state can effect transiently activated quenching.

Figure 4:
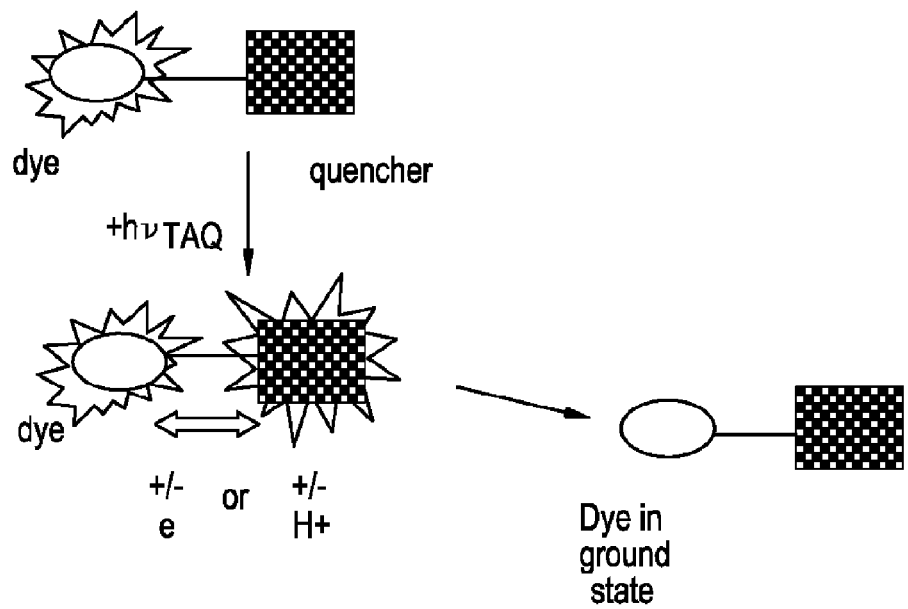
FIG. 4 illustrates an additional TAQ mechanism. The TAQ moiety in this case is a photoactivatable electron donor or acceptor or photoacid or photobase. The activated TAQ deactivates dye by a proton or electron transfer, either through-bond or through-space; for the latter confinement to a common volume rather than linkage between dye and TAQ is sufficient.

In one embodiment, the acceptor moiety is a photoactivatable electron donor or acceptor or photoacid or photobase. (FIG. 4) In this embodiment, the activated acceptor deactivates the donor by a proton or electron transfer, either thru-bond or thru-space; for the latter confinement to a common volume, rather than linkage between donor and acceptor, is sufficient. For example, in one embodiment, a fluorophore that changes its pKa by several units in the excited state (e.g., napthol) can be employed as the TAQ. In this case, the composite probe may include a pH sensitive dye as the donor, coupled to a quencher that either loses or gains protons when excited for short times. In this embodiment, the duration of the quenching efficiency and thus its overall efficiency in a repetitively excited spot, may be improved by sequestering the emitted proton in a capsule, e.g., a liposome. In this case, the liposome may include excited state proton transfer dyes as well as a donor dye. The ejection of a proton into the lumen could alter the voltage across the membrane until protons escape or recombine. Unlike transiently activated quenching by FRET, this type of quenching can persist for microseconds. The choice of transiently activated quenching mechanism can provide a higher efficiency and improved timing relative to image acquisition times.

Another mechanism of TAQ quenching is photoinduced electron transfer because many probes change their potential in the excited state. Yet another mechanism of quenching is photo-decryption of chemical species that are facile quenchers, for example, a chemical change that is photoinduced in a structure that leads to proximity between a quenching ion such as I– or Cs+ and the donor moiety. Further, spin-orbit coupling to higher Z atoms or to ground state triplets like molecular oxygen are examples of proximity-gated quenching. In this case, photoactivation of proximity is a potential transiently activated quenching process.

Another way of looking at the quench process is that a quench in one part of the spectrum may be accompanied by an increase in yield elsewhere, for example in another photophysical process or in photons of another energy. For example, transiently activated quenching that shifts spectra will quench one portion of the spectrum to supply populations of photons in other portions of the spectrum. Spectral shifts can be accomplished by altering the dye environment, e.g., changing water or extrinsic reagent access. The "solvent protection" of the dye could be photomodulated and a TAQ enhancing/accessing material in solution (e.g., I–) could do the actual quenching while the TAQ moiety actually decrypts the dye in response to light. The decryption could be steric or by charge movement such as by changing the proximity of a negative charge that would repel the 'helper' quencher, such as I–.

In another embodiment, access to the donor moiety by a helper molecule that forms an excited state complex (exciplex) could be photoinitiated. Photomodulation of charge, for example, can shift spectra because proximity to charge creates spectral shift in many organic fluorophores.

In yet another embodiment, the quench is one that alters the emission polarization (oscillation direction or emission polarization), because FRET, for example, is orientation dependent. In other words, modulation of orientation modulates FRET coupling. Also, polarized excitation and/or polarized detection can convert orientation changes into signal changes. For single photon transitions, there is typically a $\cos^2 \theta$ dependence, while for multiphoton systems, e.g., two-photon excitation, the polarization/orientation dependence is stronger. Photorientation effects such as induced dipoles and/or voltage sensitive interface probes may thus produce transiently activated quenching.

In one embodiment, the activated "quenching" process alters the kinetics of dye excited state relaxation and decay, so the temporal profile of the light is altered and various methods that probe that time profile (Stimulated Emission Microscopy (—not STED—), Stimulated Raman Spectroscopy, Transient Absorbance Spectroscopy, CARS, FLIM (Fluorescence Lifetime Microscopy)) will obtain signals that can distinguish the quenched spatial regions (e.g. original psf periphery) from unquenched (e.g. the central spot of the trimmed down psf). Thus time-dependent detection will improve spatial resolution.

In one embodiment, a composite probe comprises a donor moiety linked (e.g., covalently or noncovalently) to an acceptor moiety with a linker, wherein the donor moiety produces a donor moiety emission when excited to a donor excited state by a first wavelength of incident radiation, and the acceptor moiety is effective to couple the donor and acceptor electromagnetically and quench at least a portion of the donor moiety emission when the acceptor moiety is separately excited to an acceptor excited state by a second wavelength of incident radiation. Noncovalent linkages include hydrogen bonds, ionic bonds, Van der Waals forces and/or hydrophobic interactions. In a specific embodiment, the donor and the acceptor are covalently linked to the linker.

In one embodiment, the composite probe has the structure:
Donor-Linker-Acceptor

In specific embodiments, quenching is by absorption of the acceptor in a spectral region of the donor, excited state proton transfer between the donor and the acceptor, excited state electron transfer between the donor and the acceptor, excited state acceptor decryption of other quenching groups operating as: exciplexes, spin-orbit quenchers, free radical quenchers, contact "exchange" quenchers. A contact quencher is, for example, an acceptor covalently linked to an insulating/blocking moiety (e.g., a merocyanine, carotene or other photoisomerizing molecule) that moves out of the way of the acceptor when excited, allowing the acceptor to quench the donor. An exciplex ("excited state complex", of which "excimer, "excited state dimer" is a subclass), is a noncovalent contact interaction between the excited state of a probe and the ground state of a partner molecule (example: naphthalene, toluene) leading to a modified emission energy and yield characteristic of the briefly formed complex. A spin-orbit quencher is a contact quencher like molecular oxygen or high Z ion whose spins can change state in concordance with a spin change in the probe that transfers it from, e.g., singlet to triplet excited state, quenching the singlet. A free radical quencher employs similar spin-exchange mechanisms with unpaired electron(s). In a specific embodiment, the acceptor moiety absorbs in a spectral region of the donor emission when excited to an acceptor excited state by a second wavelength of incident radiation, in an amount effective to couple the donor and acceptor electromagnetically and quench at least a portion of the donor moiety emission.

Exemplary donor dye—TAQ acceptor pairs include FRET pairs as just discussed, TAQ made up of photoradicals, uncaged quenchers (quenchers that are ineffective when caged, that is, when bound to a caging group that inhibits absorbance, fluorescence, PET or ESPT), photoisomers, transient absorbers, and the like. Exemplary donor and acceptor fluorophores include, for example, xanthenes or peryleneimides comprising a reactive component such as isothiocyanate, maleimide, or iodoacetamide for subsequent linkage to macromolecules. An exemplary composite probe is shown in FIG. 3.

The donor and acceptor moiety can have fully independent, i.e., incoherent, activated states, or they can be coherently coupled (either to each other or to others of the same type, e.g. acceptor to acceptor). Coherent coupling can enhance the quench process as had been found for dendrimers. "Delocalization" of the exciton in a large composite TAQ may allow the absorbance of many dyes to contribute to the net absorbance of the TAQ, thus reducing power needs for psf modification.

Typical visible fluorochromes comprised of organic or organic/inorganic complexes will provide multiple absorbance/excitation energy bands and usually only a single electronic emission band. The ideal donor dye-TAQ pair may be designed with awareness of the relative gap between the first and second (or higher) states, often (for singlet states) referred to as S1, S2 and Sn. The donor dye sets a metric for efficient FRET; the emission band of the donor dye is at energy Ed. If the S0->S1 energy of the TAQ acceptor dye is more than Ed, the "quenching" beam may contribute to excitation of the donor dye in addition to its primary role. This is generally undesirable as it limits point spread function reduction. Ideally, the S0→S1 transition of TAQ should be at much lower energies than Ed. After TAQ excitation, the (relaxed) S1→(S2 or Sn) band constitutes the transient absorbance band, so the S1→(S2 or Sn) band should have strong overlap with Ed. In some cases, the S1→S2 gap can be predicted from differences between S0-S1 and S0-S2 in an absorbance graph, but excited state changes in S1 may cause shifts so the best way to choose a FRET based TAQ is to measure the transient absorbance spectrum (typically on a nanosecond timescale for ordinary dyes).

For example, in one embodiment, the donor moiety has an emission band of about 520 nm to about 600 nm (FWTM), and the acceptor moiety has an excitation gap of about 770 nm to about 810 nm in S0→S1 but 580-680 nm in S1→S2.

In one embodiment, the donor moiety is a fluorescent protein such as SNAP-tag from Covalys or HaloTag® from Promega modified with the donor and TAQ chromophores and appropriate linkages. In one embodiment, "green fluorescent protein" and related moieties can be screened for those whose S1→S2 are suitable to be transient absorbers. Alternatively, pairs of fluorescent proteins can be employed wherein the donor is a protein whose yield is proton sensitive ("proton wires" in GFP-like proteins) and the acceptor is a fluorescent protein with a proton transfer chromophore (either intrinsic or attached) (ESPT) that can be interfaced to the donor protein's 'proton sensitive' face. Fluorescent proteins such as Dronpa and Kaeda are photoswitchable. Photochromism or photoswitching refers to the ability to manipulate molecular properties using only irradition with light of an appropriate wavelength. In addition to its bright green fluorescence, Dronpa exhibits fast photoswitching between a bright and a dark state, allowing for the reversible on/off switching of the fluorescence emission. The switching of ample fluorescence in these proteins for STED has had limited success (primarily the "Citrine" family), but yield switching may be more difficult than the switching of absorbance in their excited states for STAQ.

Exemplary acceptor moieties (e.g., quench moieties) include visible dyes that quench via FRET to their excited state absorption, including: IR125, IR144, IR140, HITCI, fullerene C60, oxazine 720, some polymethine dyes (e.g., 2-[2-[3-[(1,3-dihydro-3,3-dimethyl-1-phenyl-2H-indol-2-ylidene)ethylidene]-2-phenyl-1-cyclohexen-1-yl]ethenyl]-3,3-dimethyl-1-phenylindolium perchlorate), squarylium dyes (1,3-bis-[(1,3-dihydro-1-butyl-3,3-dimethyl-2H-benzo[e]indol-2-ylidene)methyl]squaraine), or an acceptor dye that can be paired with greenish yellow, orange and red dyes. Exemplary donor moieties include ALEXA 564, Rhodamine 575, sulforhodamine, TAMRA, TEXAS RED, carboxy-X-rhodamine, lucifer yellow, eosin, green fluorescent protein, yellow fluorescent protein, and DsRed.

In specific embodiments, the composite probe is:
Rhodamine 575-linker-IR125
lucifer yellow-linker-IR125,
sulforhodamine-linker-IR125
texas red-linker-IR125
green fluorescent protein-FP-linked IR125, where FP refers to a Promega halotag protein and the link on IR125 is a haloalkane, or a Covalsys "SNAP" protein with snap-ligand linked to IR125 or peryleneimide and terrylene, or
fluorescein confined in SUV (small unilamellar vesicles, generally phospholipid) with napthol (napthol ejects protons in its excited state, fluorescein is acid quenched).

Figure 5:
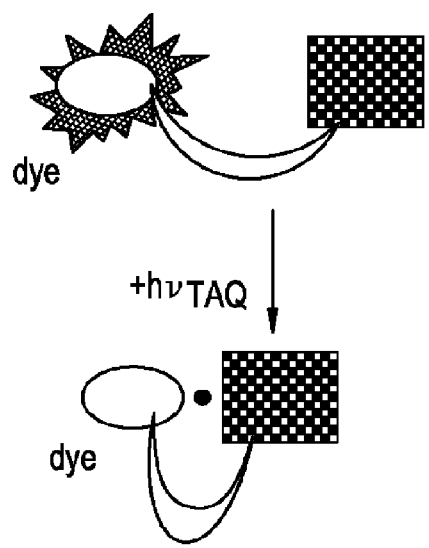
FIG. 5 illustrates an alternative STAQ mechanism. The TAQ moiety in this case is a photoactivatable linker and a quencher; the linker keeps the quencher from quenching the dye until the linker is photoactivated, changing either proximity or other variables that then permit the quencher to quench the excited dye.

The nature of linker will depend upon the particular application, point of attachment and type of conjugation desired. The linker may be attached directly to the dye, or it may be spaced away from the dye through one or more intervening atoms that serve as a spacer. The linker can be hydrophilic or hydrophobic, long or short, rigid, semirigid or flexible, depending upon the particular application. In one embodiment, the linker is a rigid linker. The linker is optionally substituted with one or more substituents or one or more additional linking groups, which may be the same or different, thereby providing a "polyvalent" linking moiety capable of conjugating with multiple molecules or substances. In one embodiment, the linker is a photoconvertable linker, that is, a linker that changes length or angle upon illumination at a chosen wavelength, thus changing orientation and proximity of donor and quencher. (FIG. 5)

A wide variety of linkers comprising stable bonds include, for example, alkyldiyls, substituted alkyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, substituted heteroaryl-heteroalkyldiyls, and the like. The linker may include single, double, triple or aromatic carbon-carbon bonds, nitrogen-nitrogen bonds, carbon-nitrogen, carbon-oxygen bonds and/or carbon-sulfur bonds, and may therefore include functionalities such as carbonyls, ethers, thioethers, carboxamides, sulfonamides, ureas, urethanes, hydrazines, etc. In one embodiment, linker has 1-20 non-hydrogen atoms selected from the group consisting of C, N, O, and S and is composed of a combination of ether, thioether, amine, ester, carboxamide, sulfonamides, hydrazide, aromatic and heteroaromatic bonds.

Choosing a linker having properties suitable for a particular application is within the capabilities of those having skill in the art. For example, where a rigid linker is desired, exemplary linkers include a rigid polypeptide such as polyproline, a rigid polyunsaturated alkyldiyl or an aryldiyl, biaryldiyl, arylarydiyl, arylalkyldiyl, heteroaryldiyl, biheteroaryldiyl, heteroarylalkyldiyl, heteroaryl-heteroaryldiyl, etc. Where a flexible linker is desired, exemplary linkers include a flexible polypeptide such as polyglycine or a flexible saturated alkanyldiyl or heteroalkanyldiyl. Hydrophilic linkers include, for example, polyalcohols or polyethers such as polyalkyleneglycols. Hydrophobic linkers may be, for example, alkyldiyls or aryldiyls.

Rhodamine dyes including a linking moiety can be conjugated to a variety of different molecules and substances using a plethora of different conjugation means. In one embodiment, conjugation is by covalent linkage. In others, the affinity of the linker and conjugation means attached to selected macromolecules is employed; e.g., the linker has biotin attached and streptavidin is the target.

In one embodiment, the linker is a rigid linker such as polyproline having a length of 15 Å to 35 Å.

An exemplary heterodimeric STAQ dye is as follows:

Rhodamine-6G - - - Pr$_6$ linker - - - IR125

In addition to dimeric STAQ composite probe constructs, dendrimeric constructs are also possible. In this embodiment, a plurality of acceptor moieties is conjugated to a single donor moiety, providing for multiple color studies at high resolution. Fluorophores can be conjugated to dendrimers with either short (e.g., direct coupling), medium (e.g., using small-molecule bifunctional linkers such as SPDP, sold by Pierce Chemical Company), or long (e.g., PEG bifunctional linkers, sold by Shearwater Polymers) linkages. Since dendrimers have surfaces with a large number of functional groups, more than one acceptor and/or donor moiety may be attached to each dendrimer. The multiple TAQ moieties may participate in homotransfer FRET or other exciton transfer activities enhancing their efficiency over individual TAQ held at equivalent distances; e.g. distant TAQ may accept excitation in the TAQ band and transfer it to more proximate (to donor) TAQ for more efficient donor quenching.

U.S. Pat. No. 6,177,414 is incorporated by reference herein for the disclosure of starburst dendrimers.

In one embodiment, the donor and the acceptor are not joined by a linker, but are rather placed in proximity in the sample, for example, by co-inclusion in vesicles, zeolites, cyclodextrins, polymeric beads, dendrimers or surface polymeric brushes. In general, the distance between the donor and the acceptor is about 10-100 Å for a FRET-based quenching mechanism, larger than 100 Å for a proton or electron-induced gradient quenching, and under 5 Å if direct electromagnetic (e.g. Marcus, Rehm-Weller or Dexter mechanisms, spin-orbit or other "contact" quenching. In one embodiment, IR125 and rhodamine 6G could, for example, both be inside a linked pair of cyclodextrin hosts, a short nanotube, or adsorbed in proximity to each other in a 20 nm polymeric bead; quenching would still occur, though likely with less efficiency and reliability than with a linker. In essence, a linker is a means of affording effective donor and acceptor proximity where proximity required is generally <10 nm for FRET-based quenching, and <1 nm for contact-based quenching.

In one embodiment, a method for irradiating a selected region of a target material comprising the composite probe described above comprises producing an exciting light beam in an optical device having a spot closely approximating its point spread function, the exciting light beam having a first wavelength in a region effective to excite the donor moiety of the composite probe to a donor excited state to produce a donor emission; producing a quenching light beam in the optical device, the quenching light beam having a second wavelength effective to excite the acceptor moiety of the composite probe to an acceptor excited state, wherein the acceptor moiety in the acceptor excited state is an excited quencher that quenches in the donor emission region; and directing the exciting light beam and the quenching light beam of radiation to overlap in the selected region of the target material to quench at least a portion of the donor emission of the donor moiety to the acceptor moiety in the selected region, wherein the quenching produces a modified point spread function in the optical device that is narrower (or otherwise more desirable) than the point spread function in the absence of the quenching beam.

In another embodiment, a method for irradiating a selected region of a target material, the method comprises providing a target material comprising a donor molecule and an acceptor molecule, wherein the donor molecule is in an amount effective to produce a donor molecule emission when excited to a donor excited state by a first wavelength of incident radiation, and the acceptor molecule is in an amount effective to couple the donor and acceptor electromagnetically and quench at least a portion of the donor molecule emission when the acceptor is separately excited to an acceptor excited state by a second wavelength of incident radiation; producing an exciting light beam in an optical device having a spot closely approximating its point spread function, the exciting light beam having the first wavelength in a region effective to excite the donor molecule of the composite probe to a donor excited state to produce a donor emission; producing a quenching light beam in the optical device, the quenching light beam having the second wavelength effective to excite the acceptor moiety of the composite probe to an acceptor excited state, wherein the acceptor moiety in the acceptor excited state is an excited quencher that quenches in the donor emission region or; and directing the exciting light beam and the quenching light beam of radiation to overlap in the selected region of the target material to quench at least a portion of the donor emission of the donor molecule in the selected region, wherein the quenching produces a modified point spread function in the optical device that is narrower than the point spread function in the absence of the quenching beam.

One advantage of the methods disclosed herein is that multicolor superresolved imaging and/or fabrication can be achieved. In one embodiment, two or more donor molecules and/or two or more transiently activated quencher molecules are employed in a single experiment. For example, two or more composite probes can be used in the same experiment. In this embodiment, the target material comprises a second composite probe, wherein the second composite probe donor moiety, the second composite probe acceptor moiety, or both is different from the donor moiety and acceptor moiety of the first composite probe.

In one case, the use of multiple transiently activated quenchers at comparable distances from the donor dye can proportionally reduce power needs. This is due to the fact that only one acceptor needs to be transiently activated to provide donor quenching. The second transiently activated quencher acts as an independent "antenna" carrying the same molar extinction coefficient, so the presence of two (or more) transiently activated quenchers increases the activation probability per illuminating photon twice (or more). For equal STAQ psf reduction efficiency, therefore, a N-TAQ (where N is the number of independent transiently activated quenchers within range) probe will require approximately N-fold less illumination.

Alternatively, the spectral properties of the transiently activated quencher may make it a quencher for a range of emissions. For example, IR125 has a transiently activated band at in the yellow to red spectrum, so broad greenish, yellow, orange or red donor dyes may have good overlap with a single transiently activated quencher. Thus, unlike traditional STED, in STAQ a single quenching laser wavelength may be able quench several donor colors, providing, for example, for multicolor superresolved video.

In one embodiment, the method further comprises detecting an optical measurement signal from the selected region of the target material. Exemplary optical measurement signals include a variable selected from timing; polarization; absorbance; a temporal correlation selected from bunching, energy and yield; a cross section for a different optical process; or a combination thereof.

As used herein, the point spread function (PSF) is response of an optical device such as a microscope to a "point source or point object", in the present case an emitting source much smaller (at least 20×) than the wavelength of light. Because of aberrations in the optics and diffraction, an optical instrument produces a "blurred" effect compared to the source which may be a single molecule. In the STAQ method, the quenching light beam, through the transiently activated quencher, modifies the peripheral population of excited donors in the region defined by the point spread function of the excitation beam and produces a smaller spot, allowing for imaging or nanofabrication of smaller structures than might be accomplished with an unmodified point spread function.

In one embodiment, an instrument suitable for carrying out the claimed method comprises an excitation source to produce an exciting light beam, a quenching source to produce a quenching light beam, an optical system for overlapping a portion of the exciting light beam and a portion of the quenching light beam and focusing the overlapped light beams onto a sample. In one embodiment, the instrument comprises a detecting unit for detecting an optical response signal generated by the sample as a result of the irradiation from the optical systems. The excitation source and the quenching source can be the same or different. In one embodiment, the optical system comprises a sample platform to hold the sample. In one embodiment, the quenched donor population is interrogated by a third light beam and changes in the optical properties of that beam report on the photochemical state of the superresolved volume.

As used herein, the term microscope is used as a shorthand notation for instruments containing an exciting light beam, a quenching light beam, an optical system and optionally a detector as described herein. While microscopes are often used to produce images of small objects, microscopes as used herein include instruments suitable for photolithography, nanofabrication, and optical digital information storage and retrieval.

In one embodiment, the method is performed on a scanning instrument. A scanning microscope, for example, is a microscope in which an image is built up point-by point by scanning a plurality of discrete spots within the sample. Scanning can be performed by moving the sample platform, the excitation beam, the quenching beam, or a combination thereof. The sample can be moved in the x-y directions to produce a substantially 2-dimensional pattern of irradiation, or optionally also in the z-direction to produce a 3-dimensional pattern of irradiation.

In one embodiment, the sample is arranged on a positioning table, with which a mechanical raster movement is carried out, at least in the direction normal to the optical axis. The device then corresponds to a raster microscope in which the sample can be scanned. In this case, an improvement in local resolution in the axial direction is especially advantageous, since improved resolution can be achieved in that direction through finer rastering. Another advantage is achieved if there is a beam-raster device for controlled scanning of the sample, with the exciting light beam and the quenching light beam between the light source and the lens. The device is used as a raster microscope in which the sample can be scanned laterally or three-dimensionally. In such a raster microscope, better local resolution can also be achieved in the lateral direction by making the "X, Y and Z" rastering smaller. In one embodiment, the laser pulses or trains of pulses are temporally coordinated with the raster scanning to permit sample changes due to quenching processes to relax back to equilibrium.

In one embodiment, the excitation light beam, the quenching light beam or both is moved relative to the sample. In another embodiment, the quenching light beam is moved laterally in the focal plane with regard to the exciting light beam. This arrangement makes the effective point spread function of the device narrower in the lateral direction. It can also be helpful if the quenching light beam is moved along the optical axis in relation to the exciting light beam. This then improves the local resolution of the device in the axial direction.

In another embodiment, there is at least one other quenching light beam coming from the light source whose intensity distribution in the focal range of the lens is different from the intensity distribution of the other quenching beams. The type of narrowing of the effective point spread function can be chosen by the spatial arrangement of the quenching light beams. Advantageously, the quenching light beams can be spatially arranged symmetrically in relation to the exciting light beam. For example, the quenching light beams can be arranged so that they generate a circular ring concentric to the exciting light beam. Here, the quenching beams can be the same distance from one another. That way, the main maximum of the intensity distribution generated by the exciting light beam is narrowed evenly, from several sides. Other arrangements of the quenching light beams are also possible.

According to one embodiment, the light source includes one or more lasers, which emit portions of light of different wavelengths. The light of one wavelength is then used as the excitation light. The wavelength of the light is selected so that the energy status of the composite fluorescent probe is excited by the light. The portion of light with the other wavelength is chosen for the quenching light. The wavelength is chosen so that the donor fluorophore can be quenched by the excited acceptor fluorophore. In one embodiment, the wavelengths for the excitation light and the quenching light are different from one another. In the event that these wavelengths are the same (at different powers), one can simply use a laser that only emits one wavelength.

In one embodiment, the light source includes at least two lasers, which emit light of different wavelengths. Then one laser is used to produce the excitation light and the other laser(s) to produce the quenching light. Several quenching light beams can be produced either with a laser, which is possible with a suitable filter or an appropriate array of mirrors, or several lasers can be used to produce one or more stimulating beams each. The use of lasers as a light source also has the advantage that light beams that can be highly localized spatially with high intensity are available.

An example appropriate to the exemplary probe is an optical parametric oscillator (e.g. "MIRA-OPO") internally doubled in frequency to generate 560 nm donor excitation; the OPO is pumped by a modelocked Ti-sapphire laser (e.g. "MIRA", both from Coherent Inc.) which also yields 777 nm light to excite the TAQ moiety.

In one embodiment, a continuous-wave laser is provided, which sends out excitation light. Using a continuous wave laser makes the arrangement less expensive. At least one laser can be provided that sends out a light pulse in a time sequence. More advantageously, a laser that sends out light pulses in a coordinated time sequence produces the quenching light synchronously with excitation pulses for the donor. The art of optical mirror and cube corner delay lines, fibers etc. is well known and can be employed to make the TAQ (quenching) pulse arrive shortly before or after the donor is excited. The TAQ excited state may have significant duration, however (typically nanoseconds) so the precise arrival time will usually not be as critical as for STED.

In one embodiment, both the excitation light and the quenching light are produced by lasers that emit light pulses in time sequence.

In another embodiment, the laser can send out a light beam with a Gaussian intensity distribution to produce the stimulating light. That way, a Gaussian spatial intensity distribution is achieved in the focal plane as well. Such an intensity distribution has the advantage that it has no auxiliary maxima that could make the resolution worse. Other Gauss-Laguerre modes may also be employed. This is especially advantageous for the quenching beams, since they can then be overlapped with the excitation beam so that they laterally overlap the main, and the quenching beam must null cleanly near the maximum of the intensity distribution of the excitation beam. In this case, any lateral maxima in the intensity distribution of the exciting light beam are suppressed because of the effect of the quenching light beams upon the effective point spread function. The quenching light beams of the intensity distribution of the excitation beam can be overlapped from outside without any new auxiliary maximum being created in the effective point spread function. In this case, a clear narrowing of the main maximum of the effective point spread function is achieved without any auxiliary maxima occurring.

In one embodiment, the light source for producing the quenching is high intensity, so that there is a nonlinear connection between that intensity and the occupation of the TAQ moiety energy state of the sample.

In one embodiment the instrument includes a time-control device, with which the detector can be turned on only directly after the pulse of the stimulating light dies. In this arrangement, if lasers that send out light pulses in a time sequence are used to produce both the excitation light and the quenching light, the time-control device can also control the lasers in such a way that a quenching light pulse is emitted as soon as an excitation light pulse has died. The detector can then be activated (or gated) with the same time-control device after the pulse of the quenching light dies. As used herein, the term "gateable" refers to the ability to activate or gate the collection of photons to enhance resolution. A simple, clean separation of the emission light of the sample is possible even when the excitation light has substantially similar or the same wavelength as the emission light. Such time gated collection may be extended to collect photons at many different intervals before or after laser illuminations; since many of the TAQ processes anticipated are dynamic, the registration and analysis of photon arrival times may be used to further enhance the imaging resolution. In the case of donut illuminated TAQ employing FRET, the lifetime of the excited state dye population decreases as one moves away from the central minimum of the spot. Thus, lifetime imaging can be used to select only the central portion of the new psf to narrow it further.

In one embodiment, the method is performed with a scanning microscope such as a confocal scanning microscope. In a conventional fluorescence microscope, the entire specimen is flooded with light from a light source. A confocal microscope, in contrast, uses point illumination and a pinhole in an optically conjugate plane in front of the detector to reduce out-of-focus information. In order to scan the sample, the stage can be translated in the x, y, and z directions while the laser illumination spot is held in a fixed position, or alternatively the beam itself can be raster-scanned across the specimen.

One embodiment of a confocal scanning microscope is described herein, but embodiments are not limited to this configuration. In one scanning confocal microscope configuration, coherent light emitted by an excitation source, typically a laser, passes through a pinhole aperture in a conjugate plane (confocal) with a scanning point on the specimen and a second pinhole aperture positioned in front of the detector (e.g., a photomultiplier tube). The laser is reflected by a dichromatic mirror and scanned across the specimen in a defined focal plane, secondary fluorescence emitted from points on the specimen (in the same focal plane) pass back through the dichromatic mirror and are focused as a confocal point at the detector pinhole aperture. Fluorescence emission that occurs at above and below the objective focal plane is not confocal with the pinhole and is not detected by the photomultiplier and does not contribute to the resulting image. Refocusing the objective in a confocal microscope shifts the excitation and emission points on a specimen to a new plane that becomes confocal with the pinhole apertures of the light source and detector.

In laser scanning confocal microscopy, the image of an extended specimen is generated by scanning the focused beam across a defined area in a raster pattern controlled by two high-speed oscillating mirrors driven by galvanometer motors. One of the mirrors moves the beam from left to right along the x lateral axis, while the other translates the beam in the y direction. After each single scan along the x axis, the beam is rapidly transported back to the starting point and shifted along the y axis to begin a new scan. The confocal image of a specimen is reconstructed, point by point, from emission photon derived signals by the photomultiplier and accompanying electronics. In some embodiments, the beams can be temporally modulated so that the transient activation of the quencher does not diminish subsequent pixels in an image; i.e. the TAQ activation can be coordinated with interleaving of line scans so the transient activation is effectively finished prior to the new interrogation of a pixel that once resided in the 'quenching zone' for some prior target pixel.

In one embodiment of a scanning microscope, the exciting and quenching beams are produced by synchronized dye lasers to tune the 570-680 nm rhodamine region. In another embodiment of a scanning microscope, a Ti-sapphire pumped OPO will be used to excite near 560 and activate TAQ quench at 775 nm.

In one embodiment, the activation of the quencher is extremely brief if the quenching pulse is ultrafast, or the quenching pulse can be longer than the quenching process but shorter than the process of superresolving.

It is to be understood that the method disclosed herein may be combined with various measures which are familiar to the person skilled in the art. These comprise in particular measures for three-dimensional resolution of the registered positions of the molecules in the specimen, i.e., for spatial resolution of these positions in the z direction as well. These measures include multi-photon excitation of the fluorescent composite probe, and using two mutually opposing objectives with high numerical aperture in 4-pi configuration for exposing the specimen to the light of the one wavelength and/or for registering the fluorescent light from the specimen. In so far as the light is then respectively focused only into one or more individual points of the plane, the plane with these points is to be scanned in all steps of the method, for example during the recording of each individual image. The focusing of the light of the one-wavelength into individual points of the specimen may advantageously be combined with confocal registering of the fluorescent light from the specimen. As an alternative the specimen may be exposed, orthogonally to the direction of the imaging of the specimen onto the sensor array, to the light of the one wavelength from which a light section is formed by a cylindrical lens. This procedure is known to the person skilled in the art as SPIM (Selective Plane Illumination). The introduction of phase plates, either electrically modulated or fixed, can be used to alter either excitation beam or STAQ quenching beam profiles in X, Y and Z. Multifocal extensions are also anticipated.

Nonlinear optics can be employed, an advantage of which is that it allows for high energy peak power to be confined to a smaller area than that achievable with linear infrared optics. In a typical nonlinear excitation, one introduces a sufficiently high power flux in an optical material to excite nonlinear behavior, meaning that the properties of the material change with the input optical power.

In one embodiment, excitation of the composite fluorescent probe is performed using multi-photon excitation. "Multiple photon excitation" means the simultaneous absorption of multiple photons by a chromophore or TAQ molecule. The method is particularly suitable for the formation of three-dimensional objects or structures having dimensions on the micro- and nanometer scale. The focused wavelength is an approximately even multiple of that required for photoactivation of the reactive species with linear optics, resulting in multi-photon excitation. Thus, two photons, at a wavelength double that required for excitation, or three long wave photons, at a wavelength triple that required for excitation, or even four photons-, at a wavelength quadruple that required for excitation of the reactive species, is used for activation.

In another embodiment, the excitation can be a multiwave mixing process, e.g., a degenerate four wave mixing process, optionally by vibrational quanta, electronic quanta, or mixtures thereof. The electromagnetic waves are optionally employed in concert with external magnetic fields or electric fields that do not oscillate as frequently as the light.

In one embodiment, the target material is a sample such as a biological sample to be imaged, for example, by fluorescence microscopy. In another embodiment, nanolithography is performed on the target material. Nanolithography means the fabrication of nanometer-scale structures, that is, patterns having at least one dimension less than 100 nm. Nanolithography includes top-down methods such as etching and bottom up methods such as fabrication, e.g., by photopolymerization. For example, the target material may be a substrate with a photoresist layer such as a composite probe in a photoresist layer of a wafer to be made into microchips. Scanning of the photoresist layer allows one to produce a pattern in the photoresist. In another embodiment, the target material is a precursor composition that is, for example, polymerizable or crosslinkable (usually by free radical or cationic mechanisms) upon photoinitiation. Photoinitiable polymerizable or crosslinkable precursor compositions will therefore ordinarily comprise an initiator for initiation of the reaction, as well as monomers, oligomers and/or polymers and/or crosslinkers capable of free radical or cationic chain propagation and chain termination steps. The initiator may or may not be covalently attached to the crosslinker, monomer, oligomer, and/or polymer. The TAQ moiety need not be directly linked to the dye; in a thin coating, for example, the proximity of TAQ and dye may be achieved by simple dilutions of the dye and TAQ moieties into appropriate matrix. The proximity would be achieved by concentration in that coating volume. In imaging applications the proximity of dye and TAQ quencher should be guaranteed with a linker since the underlying pattern is to be discovered rather than imposed, but in photolithography or photopolymerization/photoinhibition the pattern is externally imposed so random high concentration of TAQ may suffice.

In one embodiment, the sample is a biological sample to be imaged by a microscopy technique. Exemplary biological samples include cells and tissues, fixed or live, such as tissues of mammalian origin, particularly human tissues. In addition, because the composite probes can be designed to be chemically active, nanomanipulation of biomolecules, vesicles and organelles using the composite probes to, e.g. lower pH in only an attoliter volume is possible.

In one embodiment, the sample comprises a photoresist containing the dye and TAQ quencher and irradiation of the photoresist etches a pattern in the photoresist. Alternatively, irradiation can produce a photopolymerization to produce a pattern. The unquenched excited dye states present within the central part of the STAQ-modified psf are thus used to initiate polymerization or etching chemistry In one embodiment, the sample comprises a precursor composition for photopolymerization and/or photocrosslinking upon photoinitiation. In one embodiment, photoinitiable polymerizable or crosslinkable precursor compositions comprise an initiator for initiation of the reaction, as well as monomers, oligomers and/or polymers and/or crosslinkers capable of free radical or cationic chain propagation and chain termination steps. The initiator may or may not be covalently attached to the crosslinker, monomer, oligomer, and/or polymer. The composite probe may or may not be linked directly to these partners as the initiation process occurs over short (few nm) range.

Suitable photoinitiators for radical polymerization include, but are not limited to azo compounds such as azobisisobutyronitrile, peroxides such as benzoyl peroxide, aliphatic carbonyl compounds such as ketones and diketones, and aromatic diketones such as benzophenone and its derivatives, and 9-fluorenone 2-carboxylic acid. Other photoinitiation systems include, but are not limited to, redox-type photoinitiators useful in aqueous systems (e.g., ion pairs such as $Fe^{3+}OH^-$, and $Pb^{2+}Cl^-$), photosensitive dyes such as eosin, rose Bengal, and erythrosin, and transition metal derivatives such as $Mn_2(CO)_{10}$ in the presence of organic halides.

Suitable free radical polymerizable compounds include, but are not limited to crosslinkers, monomers, oligomers and/or polymers having at least one olefinic (unsaturated) bond, such as crosslinkers, monomers, oligomers and/or polymers which form polyalkylenes and halogenated polyalkylenes, polyacrylates, polymethacrylates, polyacrylamides, and styrenes.

Photoinitiators for cationic polymerization include but are not limited to triarylsulfonium and diaryliodonium salts with complex metal halide anions, and mixed arene cyclopentadienyl metal salts of complex metal halide anions, such as (6-benzene)(5-cyclopentadienyl)Fe(II) hexafluorophosphate. Suitable cationic polymerizable compounds include but are not limited to epoxides such as cyclohexene oxide.

Photopolymerizable precursor compositions may also be employed. In photopolymerizable compositions, each propagation step is effected by the incident radiation, and photopolymerization may be achieved using photo-crosslinking agents such as bisarylazides or photocross-linkable oligomers and polymers. Such oligomers and polymers contain chromophoric groups that undergo light-induced chemical bonding with each other. The chromophoric groups may be in the polymer backbone, for example a backbone chalcone group, or pendent, for example a poly(vinyl cinnamate).

The above descriptions of suitable precursors are categorized by reaction mechanism for the purposes of convenience only. It is to be recognized that other polymerizable or crosslinkable precursors, alone or in combination with other photoinitiators may also be employed, wherein the precise mechanism of polymerization (e.g., radical polymerization, single electron polymerization, or photopolymerization) is not clearly known. Thus, essentially any precursor composition which is photo-activated to form crosslinks with the fabricated construct with or without an intermediary cross-linker, and which is substantially transparent to the radiation outside the focal point is within the scope of the present disclosure. Such precursors include, but are not limited to, the above-described and other organic monomers (including dyes and chiral species), oligomers, and polymers, including biopolymers.

Biological monomers and polymers are of particular interest, including but not being limited to amino acids, peptides and proteins; fatty acids and lipids; nucleotide, oligonucleotides, and their synthetic analogues; nucleic acids; sugars and carbohydrates; bioactive agents such as cytokines, hormones, receptors, growth factors, and drugs; optically active synthetic agents (including inorganic compounds); and optically active bio-compounds such as caged compounds and fluorophores.

The STAQ methodology is used to place active (e.g., bioactive) agents into three-dimensional photo-crosslinked and/or photopolymerized gels or constructs which have controlled release, controlled degradation, and/or controlled diffusivity properties. Bioactive agents which may be so placed include, but are not limited to growth factors, nucleotides (DNA, RNA, antisense), ions, buffering agents, dyes, proteins, peptides, carbohydrates, glycosaminoglycans, enzymes, nucleotides, liposomes, cells, and drugs. Diffusion of the agent or agents out of the construct is adjusted to effect controlled release, or to expose or otherwise bring the entrapped agent or agents to the construct surface or other interface to enable bioactivity. Diffusion is controlled by one or a combination of methods, for example by control of the affinity of the agent or agents for the construct, control of the degree of crosslink density of the construct, or control of the rate of degradation of the construct. Control of the degree of affinity of the agent or agents for the construct may be achieved by appropriate selection of the construct composition, e.g., backbone and/or crosslink compositions. Use of differing cross-linking moieties allows adjustment of relative affinities of two or more agents. Entrapment of agents having different construct affinities allows controlled release at different rates.

Control of diffusion and degradation properties is most readily achieved in a chemically uniform gel by locally varying the cross-link or polymerization density. This may be achieved by varying illumination time, intensity (photon energy density), and/or by altering gel architecture, including variation of the gel's spatial dimensions, addition of overlayers of gels without entrapped reagents, and other three-dimensional patterning. Control of diffusion and degradation can also be achieved by varying gel chemistry, such as by varying cross-link chemistry, using different monomers, and by altering the rate of polymerization or cross-linking by changing other reactant constituents. FRET is a mechanism describing energy transfer between two chromophores. A donor chromophore, initially in its electronic excited state, may transfer energy to an acceptor chromophore (in proximity, typically less than 10 nm) through nonradiative dipole-dipole coupling. Certain FRET assays will benefit from the ability to turn FRET on and off in the STAQ fashion. For example, such switching may allow in situ calibration of donor brightness without FRET/prior to FRET, or induction of different levels of FRET (and consequent the ability to better quantify stoichiometry).

In another embodiment, irradiation of a substrate comprising a donor molecular and an acceptor molecule, such as a composite probe, can be used as a means of nanoscale perturbation within cells and biomolecules on the target material. For example, the narrowed point spread function irradiation can be used to initiate local biochemical reactions between biomolecules on the substrate. In addition, the narrowed point spread function can be used to provide sub-diffraction limit local release of agents in cells. For example, the release of Rose Bengal-linker-IR125 photosensitized free radicals might be targeted to only mitochondria or nuclei in cells.

In one embodiment, a fluorescence energy transfer method, comprises providing a target material comprising the composite probe described herein; producing an exciting light beam having the first wavelength in a region effective to excite the donor molecule of the composite probe to a donor excited state to produce a donor emission; producing a quenching light beam having the second wavelength effective to excite the acceptor moiety of the composite probe to an acceptor excited state, wherein the acceptor moiety in the acceptor excited state is an excited quencher that quenches in the donor emission region; and monitoring the change in fluorescence energy transfer between the donor and the acceptor in the presence of both the exciting light beam and the quenching light beam; wherein the donor moiety and the acceptor moiety are both fluorescent moieties.

The disclosure is illustrated by the following non-limiting examples:

EXAMPLES

Example 1

Synthesis of Rhodamine 6G-Gly-Pro-Pro-Pro-OH

Synthesis of H-Gly-Pro-Pro-Pro-2Cl Trityl resin (HL31): The peptide was assembled on CEM liberty peptide synthesizer using Fmoc chemistry at 0.25 mmol scale. 362 mg of H-Pro-2 Cl-Trt resin with substitution level of 0.69 mmol/g was used. After the synthesis, the resin was transferred to a manual vessel, washed with DCM, MeOH and dried. 626 mg of the dark brown resin was obtained.

Synthesis of Rhodamine-Gly-Pro-Pro-Pro-2Cl Trityl resin (HL33): To Rhodamine 19 perchloride (100 mg, 0.19 mmol) in DMF (1 mL) was added HBTU (72 mg, 0.19 mmol) and DIEA (33 µL, 0.19 mmol). The reaction mixture was stirred in RT for 2 h. Half of the mixture was added to HL 31 (0.05 mmol) in 1 mL DMF and the resin was shaken for an hour. The remaining of the reaction mixture was added to the resin and shaken for an hour. The solution was filtered off and the resin was washed with DMF (3×10 mL), DCM (3×10 mL) and MeOH (3×10 mL). The resin was dried in vacuum (HL 33).

Synthesis of Rhodamine-Gly-Pro-Pro-Pro-OH (HL34): To Rhodamine-Gly-Pro-Pro-Pro-2Cl Trityl resin (HL33) in DCM (10 mL) was added TFA (1 mL). The resin turned green. It was stirred for an hour. The filtrate was collected and taken to dryness. APCI-LC-MS demonstrated the formation of the desired peptide of a MW of 763 (HL34).

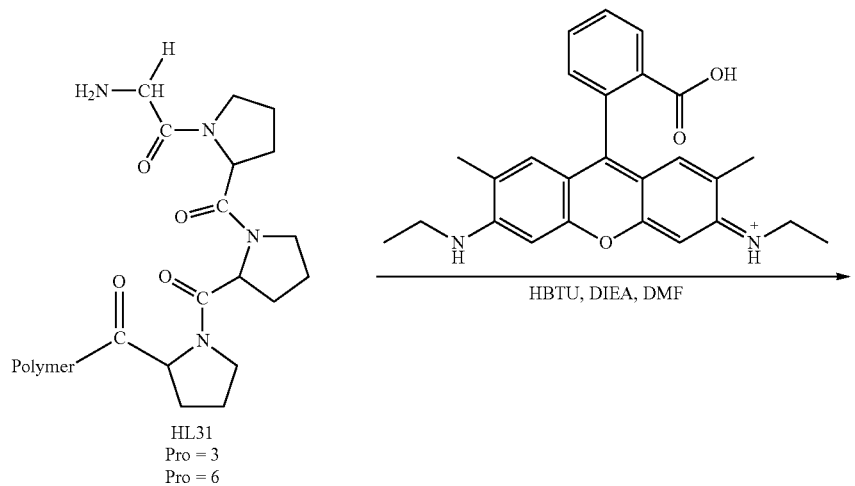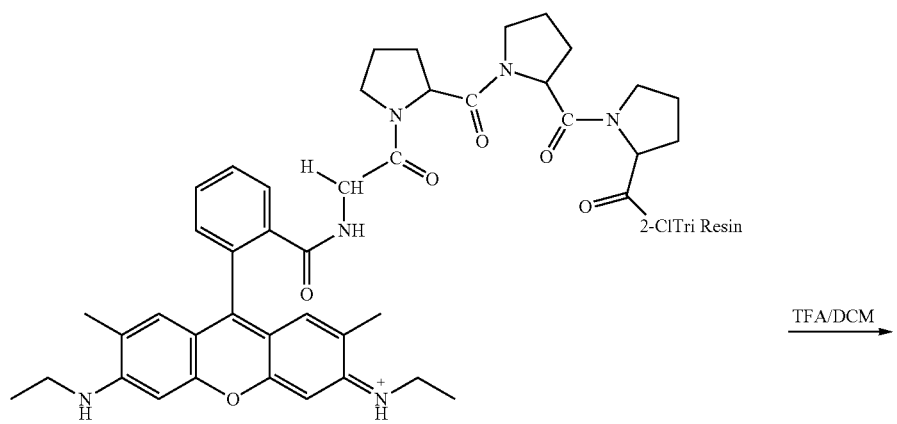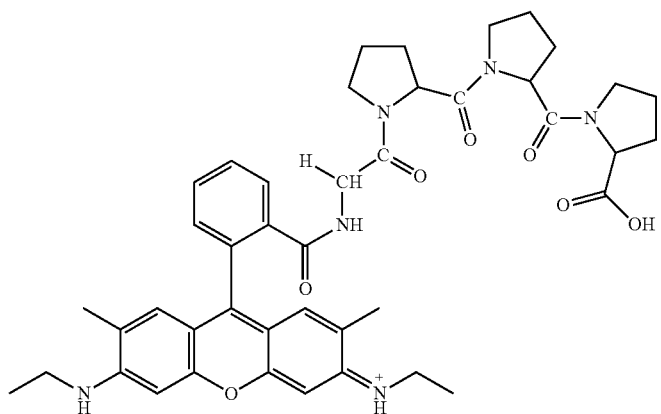

Example 2

Molecular Modeling Simulations for FRET Linker Optimization

1st Step: Building the three different components.

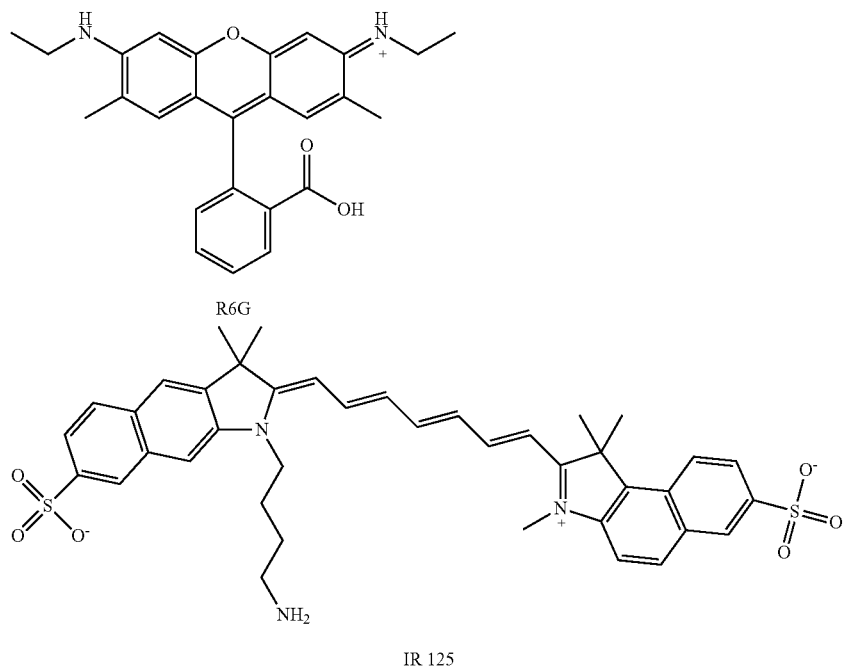

R6G

IR 125

The two dyes (IR 125 and R6G) were built from their basic components (single aromatic rings, sulfonic groups, etc.) and then minimized using MacroModel's default Molecular Mechanics minimization. The n=6 polyproline linker was generated using MacroModel's amino acid fragments and it's grow function. All prolines were joined using trans geometry and phi and psi angles reported for left-handed helices. These specifications were chosen because polyproline is usually believed to have a mainly trans geometry which forms a left-handed helix. There is some evidence that there may be kinks in polyproline chains which are due to interspersed prolines with cis conformations, however, this was not dealt with in the current study.

2nd Step: Building and minimizing the n=6 system: The two dyes were attached to their respective ends of the n=6 polyproline linker using the "Connect & Fuse" function in MacroModel (this function joins the selected atoms and correctly adjusts the number of attached hydrogen so that the atoms remain neutral and uncharged). The IR125 fragment was attached to the C-terminus of the linker and the R6G fragment was attached to the N-terminus. The system was then minimized as before.

3rd Step: Dynamics simulations for the n=6 system: Molecular dynamics simulations were run, using water as an implicit solvent, on the minimized n=6 structure. The system was equilibrated for 20 ps, and then the dynamics simulations were run for 500 ps using a 1.5 fs time step. The average distance found for the linker in the n=6 system, based on the 100 structures saved during the simulation was 19.5 Å.

4th Step: Building and dynamics simulations for the n=3 system: The three middle prolines were deleted from a partially minimized n=6 structure and the two sides of the molecule were recombined, using the Connect & Fuse function, to form a system with an n=3 polyproline linker. This system was then minimized as above and the minimized structure was then run through several MacroModel conformational searches to determine if this was the most common conformation. The conformational searches used water as an implicit solvent. There was little change in the structures found by the conformational search so the dynamics simulation used the same structure that the conformational search was started from. The simulation was run with the same specifications as the simulation for the n=6 system. The average distance found for the linker in the n=3 system was about 1 nm (9.5 Å).

The minimization of this system changed the orientation of the R6G dye similarly to the change seen in the minimization of the n=6 system. The linker itself also exhibited little change during this minimization. However, the orientation of the IR125 dye in the minimized systems is different. The R6G dye again folded over so that it is closer to the linker while the O—C—N—H dihedral changed from −175.7° to 179.7°. Initially the IR125 dye was perpendicular to the linker and the C—C—C—N dihedral which changed drastically in the n=6 system after minimization changed very little, from −177.8° to −174.6° in the n=3 system. The dihedral connecting the dye to the linker (C—N—C—C) changed drastically in this minimization, going from −178.7° to 0.0°, this change brought one side of the dye closer to the R6G and the other side further away, as opposed to the minimization of the n=6 system which made the distances between the R6G and the two sides of the IR125 much more equal. This can be seen by examining the distance from the oxygen in the xanthene moiety of the R6G dye to the sulfonic groups in the IR125, the un-minimized distances are 17.271 Å and 12.287 Å while the distances in the minimized system are 5.913 Å and 24.071 Å.

The n=6 system will be a more optimal FRET system because the main interaction between the dyes will be through the linker. The n=3 system will be less optimal because, based on the shrinking distance between the oxygen of the xanthene moiety and one of the sulfonyl groups, the dyes interact beyond the expected FRET system.

Example 3
Design and Synthesis of Luminescent Probes

Study parameters include: a) dye modification to link them together and b) optimum linker length which plays role in the efficient energy transfer in FRET, hence different length of linkers will be synthesized. The dyes will also be investigated by molecular dynamics (MD) simulations in order to gain information on their orientation and the distance between them.

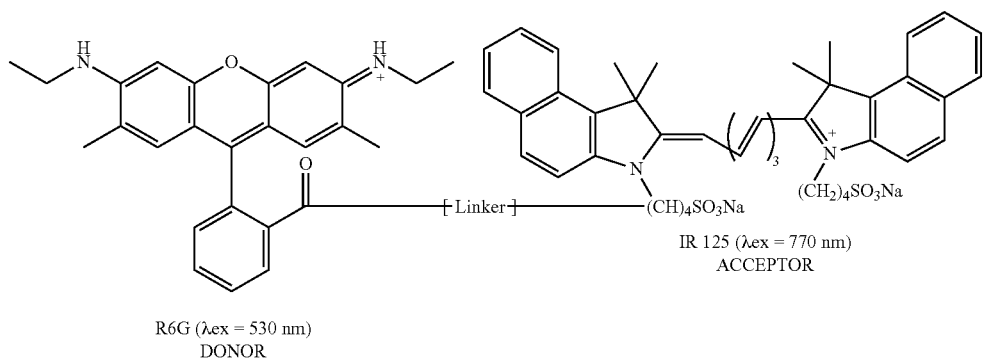

The dye pair will be linked via polyproline (rigid linker) to give an appropriate FRET distance (1-10 nm). 5 to 6 proline residues in a linker should be within the FRET distance and have efficient energy transfer, hence initially the FRET design will incorporate 6 proline residues and further optimization of linker length will be done if needed. The polyproline with n:=6 residues will be synthesized on peptide synthesizer. The dyes will be modified as well; Instead of Rhodamine-6G, commercially available aminoethyl-R6G from Sigma Aldrich will be linked with modified IR125 dye as shown below. The synthesis of modified IR125 is illustrated in Scheme 1.

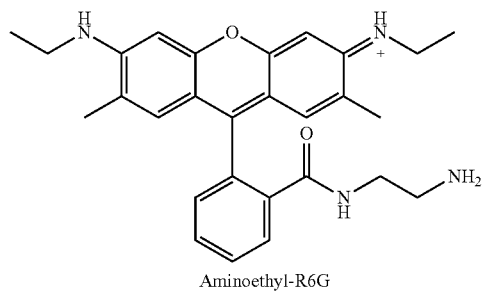

Aminoethyl-R6G

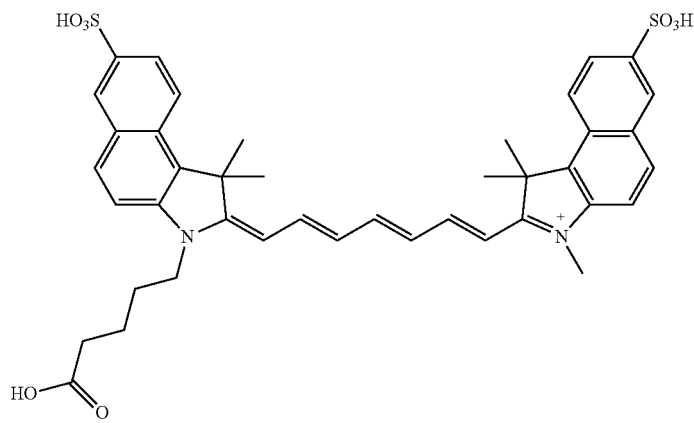

Modified IR125

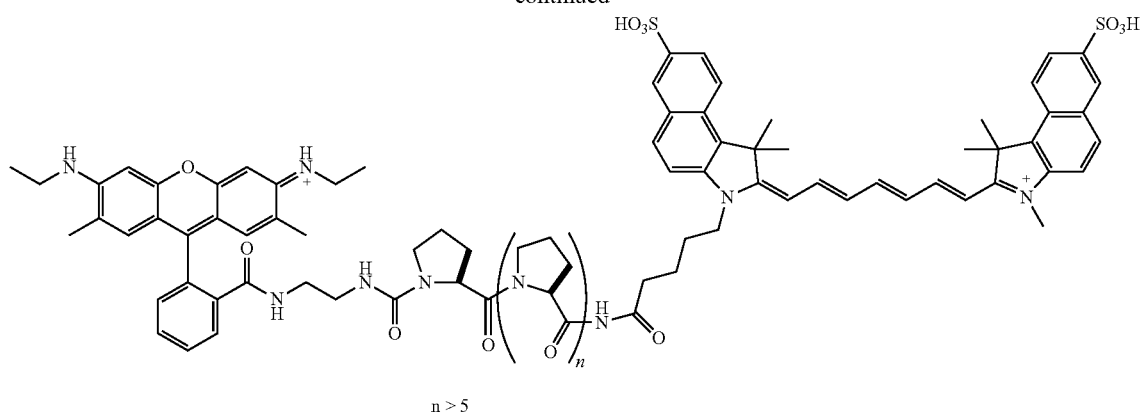
Aminoethyl-R6G linked with modified IR125
Scheme 1
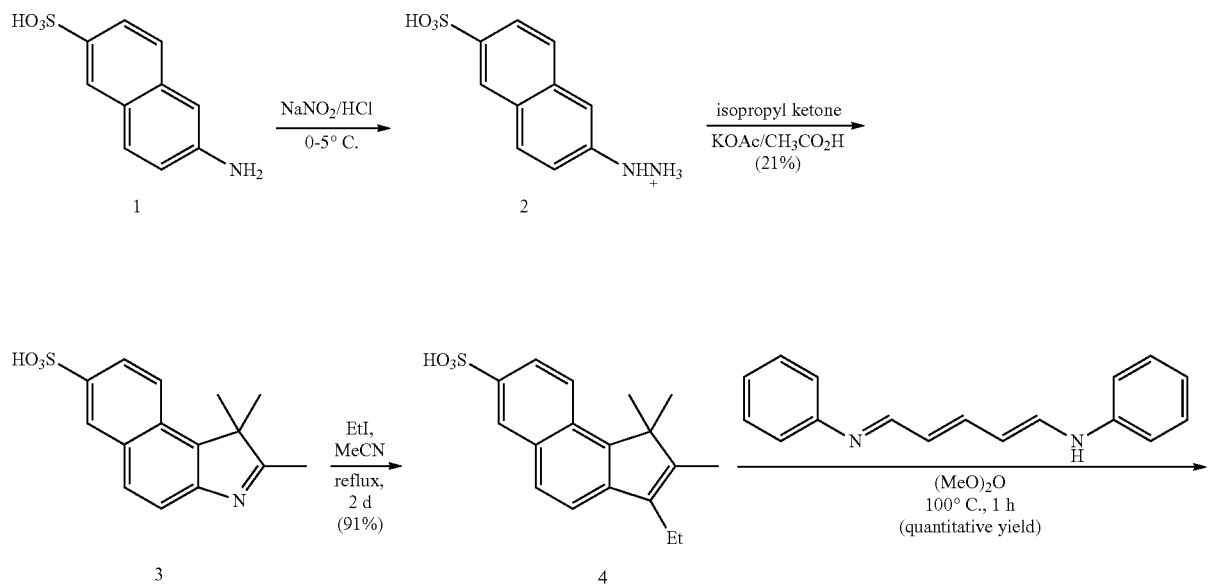
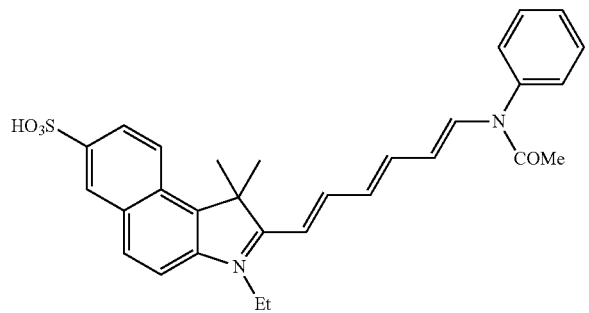

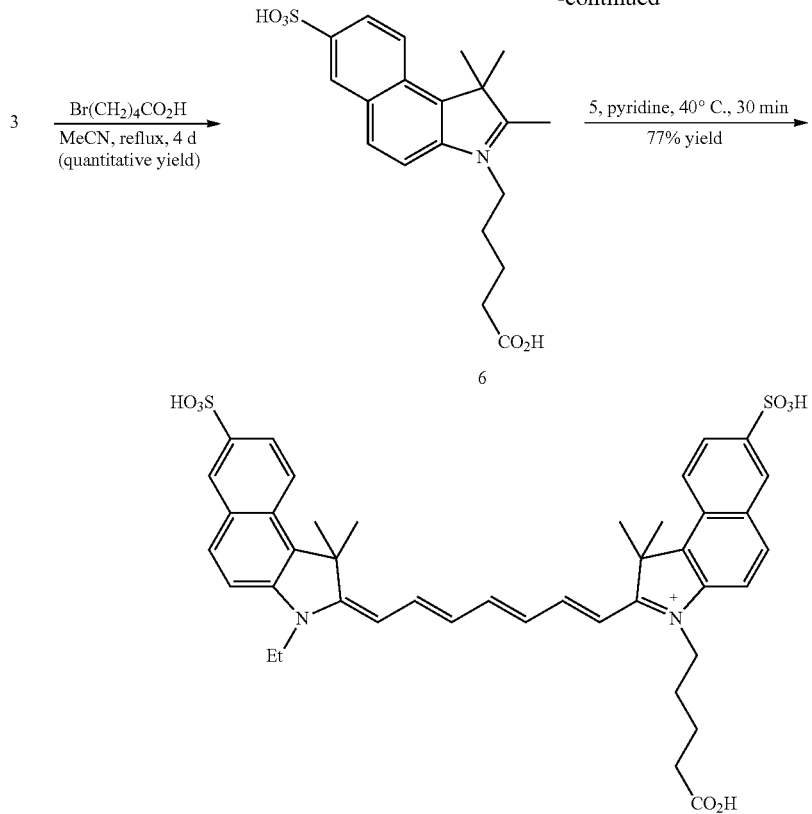

Figure 6A:
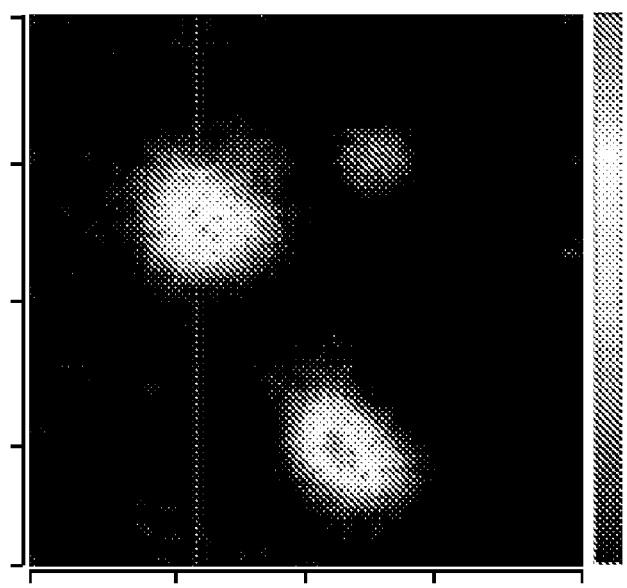
FIG. 6 shows an exemplary STAQ experiment imaging subresolution beads labeled with a STAQ dye.
Figure 6B:
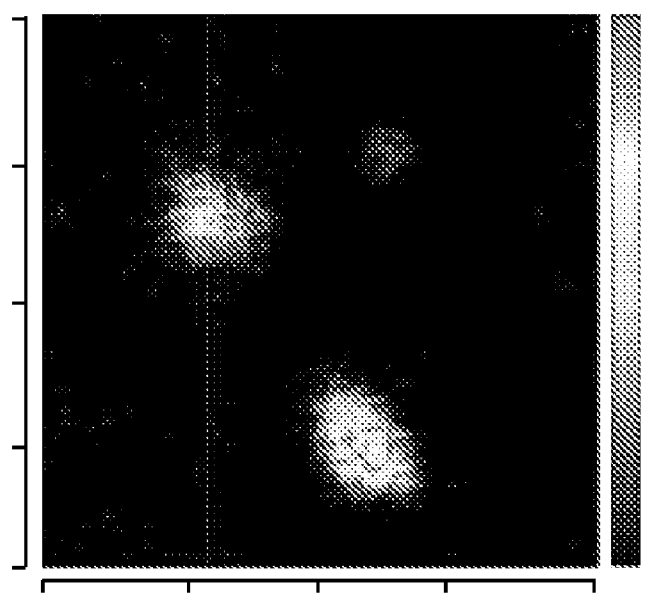

As a proof of concept experiment, subresolution (20 nm) latex beads were labeled with an amine reactive version of STAQ dye Rhodamine-6G - - - $Pr_6$ linker - - - IR125, and imaged. (FIG. 6) The donut beam was formed through the combination of a vortex phase plate (RPI, Inc) and 100× objective; about 60 mW of 775 nm light reached the donut. The images of individual STAQ labeled beads lacking a quenching illumination were over 300 nm wide; with the STAQ beam on the apparent width fell below 80 nm, although this narrow feature was superimposed on an unmodified psf (point spread function) "pedestal". Control beads labeled with Rhodamine rather than STAQ do not narrow, so we know we are not doing STED.

Thus, while the superresolved imaging was successful, there was a persistent background in these experiments. Initially it was believed that our picosecond laser was reexciting some dye molecules in the donut region due to two-photon absorbance, creating the background pedestal. Added temporal dispersion did not solve the problem, however. A line scan revealed that the central feature of the donor emission peak is being quenched in addition to the spatial edges and we surmise some of the STAQ dyes fail to perform. Without being held to theory, it is believed that the STAQ dyes may have a "kappa-squared" problem, that is, because the dye and the quencher are adsorbed to beads at various rigid angles, some of the dyes may have low or zero FRET to TAQ. Other possible problems are chemically damaged or aggregated TAQ molecules. It is also possible that the TAQ moiety could be self-quenching and turning off the quenching path too soon.

Figure 7:
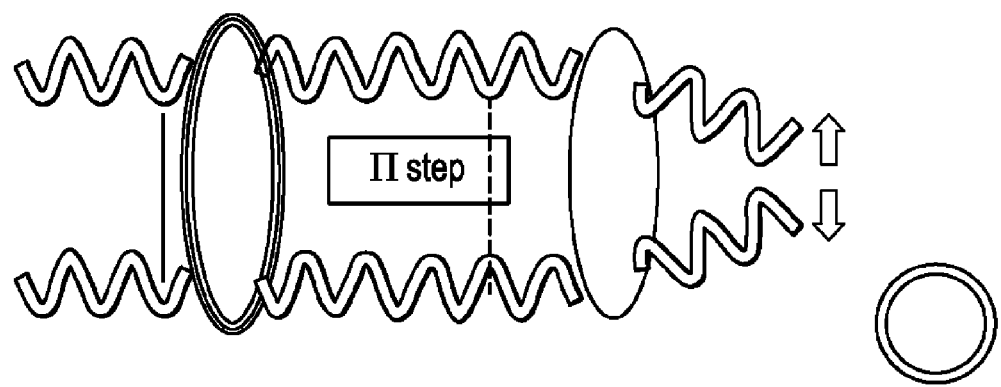
FIG. 7 shows the spiral phase plate that is used for the "donut" beam that, for high NA objectives should be accompanied by an azimuthal polarizer.

A power series analysis on larger beads confirmed the undesirable quenching of the narrow central peak. (data not shown) In order to reduce this central peak quenching, the spiral phase plate that is used for the "donut" beam should be accompanied by an azimuthal polarizer, since radial polarization has a longitudinal component after focusing that does not properly phase-cancel. (FIG. 7) More complete cancelling of the spiral beams at the focus should prevent quenching of the desired central peak.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The term wt % refers to percent by weight. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A super-resolution method for irradiating a selected region of a target material comprising a composite probe of, wherein the composite probe comprises a donor moiety linked to an acceptor moiety with a linker, wherein the donor moiety produces a donor moiety emission when excited to a donor excited state by a first wavelength of incident radiation, and the acceptor moiety is effective to couple the donor and acceptor electromagnetically and quench at least a portion of the donor moiety emission when the acceptor moiety is separately excited to an acceptor excited state by a second wavelength of incident radiation, the method comprising:

producing an exciting light beam in an optical device having a spot closely approximating its point spread function, the exciting light beam having a first wavelength in a region effective to excite the donor moiety of the composite probe to a donor excited state to produce a donor emission;

producing a quenching light beam in the optical device, the quenching light beam having a second wavelength effective to excite the acceptor moiety of the composite probe to an acceptor excited state, wherein the acceptor moiety in the acceptor excited state is an excited quencher that quenches in the donor emission region, directing the exciting light beam and the quenching light beam of radiation to overlap in the selected region of the target material to quench at least a portion of the donor emission of the donor moiety in the selected region, wherein the quenching produces a modified point spread function in the optical device that is narrower than the point spread function in the absence of the quenching beam, and producing an image of the selected region of the target material, fabricating a structure in the selected region of the target material, etching the selected region of the target material, or producing a perturbation in the selected region of the target material.

2. The method of claim 1, wherein quenching is by absorption, proton transfer, electron transfer, spin-orbit coupling, or steric decryption.

3. The method of claim 1, further comprising detecting an optical measurement signal from the selected region of the target material.

4. The method of claim 3, wherein the optical measurement signal includes a variable selected from timing; polarization; absorbance; a temporal correlation selected from bunching, energy and yield; a cross section for a different optical process; or a combination thereof.

5. The method of claim 1, further comprising scanning a plurality of selected regions to produce the image or a photopolymerization pattern.

6. The method of claim 1, further comprising scanning a plurality of selected regions and etching a pattern into the target material.

7. The method of claim 1, wherein the target material comprises one or more biological molecules and/or cells, and irradiating produces a nanoscale perturbation in the biological molecules and/or cells.

8. The method of claim 1, wherein the nanoscale perturbation produces a biochemical reaction.

9. The method of claim 1, wherein the target material comprises a second composite probe, and wherein the second composite probe donor moiety, the second composite probe acceptor moiety, or both is different from the donor moiety and acceptor moiety of the first composite probe.

10. The method of claim 1, further comprising raster scanning the target material, the exciting light beam or the quenching light beam to produce a plurality of selected regions.

11. The method of claim 1, wherein the acceptor moiety of the composite probe absorbs in a spectral region of the donor emission when excited to an acceptor excited state by a second wavelength of incident radiation, in an amount effective to couple the donor and acceptor electromagnetically and quench at least a portion of the donor moiety emission.

12. The method of claim 1, wherein the linker of the composite probe has a length of 15 to 35 Å.

13. The method of claim 1, wherein the linker of the composite probe is a flexible linker.

14. The method of claim 1, wherein the linker of the composite probe is a rigid linker.

15. The method of claim 14, wherein the linker of the composite probe is a polyproline linker having a length of 15 to 35 Å.

16. The method of claim 1, wherein the donor moiety of the composite probe is derived from rhodamine 60, ALEXA 564, Rhodamine 575, sulforhodamine, TAMRA, TEXAS RED, carboxy-X-rhodamine, lucifer yellow, eosin, green fluorescent protein, yellow fluorescent protein, or DsRed.

17. The method of claim 1, wherein the acceptor moiety of the composite probe is derived from IR125; IR144; IR140; HITCI; fullerene C60; oxazine 720; 2-[2-[3-[(1,3-dihydro-3,3-dimethyl-1-phenyl-2H-indol-2-ylidene)ethylidene]-2-phenyl-1-cyclohexen-1-yl]ethenyl]-3,3-dimethyl-1-phenylindolium perchlorate); or (1,3-bis-[1,3-dihydro-1-butyl-3,3-dimethyl-2H-benzo[e]indol-2-ylidene)methyl]squaraine).

18. The method of claim 1, wherein the donor moiety of the composite probe is excited to the donor excited state by the first wavelength of incident radiation in the region of about 470 to about 570 nm, and the acceptor moiety is excited to the acceptor excited state by the second wavelength of incident radiation in the region of about 750 to about 800 nm.

19. The method of claim 1, wherein the composite probe is a dendrimer comprising a plurality of the acceptor moieties covalently bound to a single donor moiety.

20. A super-resolution method for irradiating a selected region of a target material, the method comprising:

providing a target material comprising a donor molecule and an acceptor molecule, wherein the donor molecule is in an amount effective to produce a donor molecule emission when excited to a donor excited state by a first wavelength of incident radiation, and the acceptor molecule is in an amount effective to couple the donor and acceptor electromagnetically and quench at least a portion of the donor molecule emission when the acceptor is separately excited to an acceptor excited state by a second wavelength of incident radiation;

producing an exciting light beam in an optical device having a spot closely approximating its point spread function, the exciting light beam having the first wavelength in a region effective to excite the donor molecule to a donor excited state to produce a donor emission;

producing a quenching light beam in the optical device, the quenching light beam having the second wavelength effective to excite the acceptor moiety to an acceptor excited state, wherein the acceptor moiety in the acceptor excited state is an excited quencher that quenches in the donor emission region;

directing the exciting light beam and the quenching light beam of radiation to overlap in the selected region of the target material to quench at least a portion of the donor emission of the donor molecule in the selected region, wherein the quenching produces a modified point spread function in the optical device that is narrower than the point spread function in the absence of the quenching beam, and producing an image of the selected region of the target material, fabricating a structure in the selected region of the target material, etching the selected region of the target material, or producing a perturbation in the selected region of the target material.

21. The method of claim 20, wherein quenching is by absorption, proton transfer, electron transfer, spin-orbit coupling, or steric decryption.

22. The method of claim 20, further comprising detecting an optical measurement signal from the selected region of the target material.

23. The method of claim 22, wherein the optical measurement signal includes a variable selected from timing; polarization; absorbance; a temporal correlation selected from bunching, energy and yield; a cross section for a different optical process; or a combination thereof.

24. The method of claim 22, further comprising scanning a plurality of selected regions to produce the image or a photopolymerization pattern.

25. The method of claim 20, further comprising scanning a plurality of selected regions and etching a pattern into the target material.

26. The method of claim 20, wherein the target material comprises one or more biological molecules and/or cells, and irradiating produces a nanoscale perturbation in the biological molecules and/or cells.

27. The method of claim 20, wherein the nanoscale perturbation produces a biochemical reaction.

28. he method of claim 20, wherein the target material comprises a second donor molecule, a second acceptor molecule, or both that is different from the donor molecule and/or the acceptor molecule.

29. The method of claim 20, further comprising raster scanning the target material, the exciting light beam or the quenching light beam to produce a plurality of selected regions.

30. The method of claim 20, wherein quenching is by absorption of the acceptor in a spectral region of the donor, excited state proton transfer between the donor and the acceptor, excited state electron transfer between the donor and the acceptor, excited state acceptor decryption of other quenching groups operating as exciplexes, spin-orbit quenchers, free radical quenchers, contact "exchange" quenchers.

31. The method of claim 20, wherein the acceptor molecule absorbs in a spectral region of the donor emission when excited to an acceptor excited state by a second wavelength of incident radiation, in an amount effective to couple the donor and acceptor electromagnetically and quench at least a portion of the donor molecule emission.

32. The method of claim 20, wherein the donor molecule is rhodamine 60, ALEXA 564, Rhodamine 575, sulforhodamine, TAMRA, TEXAS RED, carboxy-X-rhodamine, lucifer yellow, eosin, green fluorescent protein, yellow fluorescent protein, or DsRed.

33. The method of claim 20, wherein the acceptor molecule is IR125, IR144, IR140, HITCI, fullerene C60, oxazine 720, 2-[2-[3-[(1,3-dihydro-3,3-dimethyl-1-phenyl-2H-indol-2-ylidene)ethylidene]-2-phenyl-1-cyclohexen-1-yl]ethenyl]-3, 3-dimethyl-1-phenylindolium perchlorate), or (1,3-bis-[(1,3-dihydro-1-butyl-3,3-dimethyl-2H benzo[e]indol-2-ylidene) methyl]squaraine).

34. The method of claim 20, wherein the donor molecule is excited to the donor excited state by the first wavelength of incident radiation in the region of about 470 to about 570 nm, and the acceptor molecule is excited to the acceptor excited state by the second wavelength of incident radiation in the region of about 750 to about 800 nm.

35. A time-gated fluorescence energy transfer method, comprising:

providing a target material comprising a composite probe, wherein the composite probe comprises a donor moiety linked to an acceptor moiety with a linker wherein the donor moiety produces a donor moiety emission when excited to a donor excited state by a first wavelength of incident radiation, and the acceptor moiety is effective to couple the donor and acceptor electromagnetically and quench at least a portion of the donor moiety emission when the acceptor moiety is separately excited to an acceptor excited state by a second wavelength of incident radiation;

producing an exciting light beam having the first wavelength in a region effective to excite the donor molecule of the composite probe to a donor excited state to produce a donor emission;

producing a quenching light beam having the second wavelength effective to excite the acceptor moiety of the composite probe to an acceptor excited state, wherein the acceptor moiety in the acceptor excited state is an excited quencher that quenches in the donor emission region; and monitoring the change in fluorescence energy transfer between the donor and the acceptor in the presence of both the exciting light beam and the quenching light beam; and collecting photons either before or after producing an exciting light beam or producing a quenching light beam wherein the donor moiety and the acceptor moiety are both fluorescent moieties, and producing an image of at least a portion of the target material.

36. The method of claim 35, wherein quenching is by absorption, proton transfer, electron transfer, spin-orbit coupling, or steric decryption.

37. The method of claim 35, further comprising detecting an optical measurement signal from the selected region of the target material.

38. The method of claim 37, wherein the optical measurement signal includes a variable selected from timing; polarization; absorbance; a temporal correlation selected from bunching, energy and yield; a cross section for a different optical process; or a combination thereof.

39. The method of claim 35, wherein the target material comprises a second donor molecule, a second acceptor molecule, or both that is different from the donor molecule and/or the acceptor molecule.

40. A method for irradiating a selected region of a target material, the method comprising:

providing a target material comprising a donor molecule and an acceptor molecule, wherein the donor molecule is in an amount effective to produce a donor molecule emission when excited to a donor excited state by a first wavelength of incident radiation, and the acceptor molecule is in an amount effective to couple the donor and acceptor electromagnetically and quench at least a portion of the donor molecule emission when the acceptor is separately excited to an acceptor excited state by a second wavelength of incident radiation;

producing an exciting light beam in an optical device having a spot closely approximating its point spread function, the exciting light beam having the first wavelength in a region effective to excite the donor molecule to a donor excited state to produce a donor emission;

producing a quenching light beam in the optical device, the quenching light beam having the second wavelength effective to excite the acceptor moiety to an acceptor excited state, wherein the acceptor moiety in the acceptor excited state is an excited quencher that quenches in the donor emission region; and varying the time and/or intensity of the quenching light beam to turn fluorescence energy transfer on or off in the selected region of the target material.

* * * * *